United States Patent [19]

Hoskinson et al.

[11] 4,354,977
[45] Oct. 19, 1982

[54] PHOSPHONOTHIOATE IMMUNOGENS

[75] Inventors: Ronald M. Hoskinson, Normanhurst; Ronald I. Cox, Beecroft; Michael S. F. Wong, North Epping, all of Australia

[73] Assignee: Commonwealth Scientific and Industrial Research Organization, Campbell, Australia

[21] Appl. No.: 129,450

[22] Filed: Mar. 11, 1980

[30] Foreign Application Priority Data

Mar. 15, 1979 [AU] Australia .............................. PD8046

[51] Int. Cl.$^3$ ................................................ C07J 1/00
[52] U.S. Cl. ............................ 260/397.4; 260/397.5; 260/112 R; 424/1
[58] Field of Search ............................ 260/397.4, 397.5

[56] References Cited

FOREIGN PATENT DOCUMENTS 920639  3/1963  United Kingdom ............. 260/397.5
1317373 5/1973  United Kingdom ............. 260/397.5

*Primary Examiner*—Elbert L. Roberts

*Attorney, Agent, or Firm*—Millen & White

[57] ABSTRACT

Novel phosphonothioate compounds of the general formula

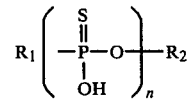

wherein
  $R_1$ is lower alkyl
  $R_2$ is a steroid residue which is linked to the rest of the molecule through any carbon atom which is not one of the carbon atoms forming a ring junction, or through a side chain carbon atom, and
  n is 1 to 4, are disclosed as well as the use of these compounds as immunogenic haptens.

Immunogenic hapten-protein complexes and conjugates of these phosphonothioate compounds and of steroid phosphates are also disclosed.

14 Claims, No Drawings

PHOSPHONOTHIOATE IMMUNOGENS

This invention relates to novel haptens and to hapten-protein complexes and conjugates. It is concerned with their use in preparing highly specific antisera and to the use of such antisera in radioimmunoassays.

As commonly used in the art of immunology, the term "hapten" refers to small molecules which are not in themselves immunogenic but which, when chemically linked to an immunogenic macromolecule, can stimulate the generation of antibodies in a mammal that are reactive to the hapten-macromolecule conjugate and to the hapten itself. Such is the meaning of the term "hapten" as used in this invention.

Many small molecules can be used as haptens to promote the formation of anti-hapten antibody, and, of these, certain naturally-occurring biologically active substances, such as steroid hormones, biogenic amines, vitamins and synthetic drugs of various classes have received much attention. This is because immunization of mammals with the conjugates such substances form with immunogenic macromolecules is a means of raising hapten-binding antisera of value in radioimmunoassay procedures, and is also a means of effecting hapten-dependent physiological changes in the immunized mammals.

Among the substances mentioned, the esters of steroidal alcohols or of phenolic steroids with sulphuric acid are of particular interest because it is in the "sulphate" form that many of the steroids of interest occur naturally. Additionally, steroid sulphates are often quantitatively the largest component of the steroidal compounds circulating in the blood, and it is to the sulphate form that exogenously administered steroid alcohols or phenolic steroids may be transformed in vivo in mammals.

Unfortunately, attempts to produce antisera specific to steroid sulphates have until now been seriously hampered by the chemical instability of the sulphates in vitro and by their susceptibility to attack by enzymes, including sulphatases, in vivo. The present invention, which is mainly directed to overcoming this problem, is based on the discovery that steroid alcohols or phenolic steroids, when substituted with particular functional groups bearing certain steric and electronic similarities to steroid sulphate esters, can be used to generate antisera specific to the sulphate ester of the parent steroid as well as to the alternatively functionalized steroid derivative. The functional groups in question are derived from certain phosphorus-containing acids and the haptens of this invention are esters of phenolic steroids or steroid alcohols with such acids. Many of the haptens described herein, and all of their complexes and conjugates with proteins, are believed to be novel.

As the subject haptens may be said to structurally mimic the sulphate esters, they will be called herein "sulphate mimics". Their outstanding value resides in the fact that many of them are more stable in vitro and in vivo than their sulphate ester counterparts, and thus they lend themselves to the preparation of antisera by relatively simple and convenient techniques which hitherto it has not been possible to employ in this area of immunology.

DETAILED DISCUSSION

According to this invention preferred classes of hapten are the monoesters of phenolic steroids or of steroid alcohols with lower alkylphosphonothioic acids. They have the general formula:

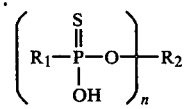

where
- $R_1$ is a lower alkyl
- $R_2$ is a steroid residue which is linked to the rest of the molecule through any carbon atom which is not one of the carbon atoms forming a ring junction, or through a side chain carbon atom, and n is 1–4.

A further class of sulphate mimic embraced by this invention comprises the monoesters of phenolic steroids or steroid alcohols with phosphoric acid, substances otherwise known as the steroid phosphates. In the case of the steroid lower alkylphosphonothioates or the steroid phosphates, the phosphorus-containing function structurally mimics the sulphate moiety of corresponding steroid sulphates in size, stereochemistry and ionizable structure at physiological pH.

As with many haptens, the steroid lower alkylphosphonthioates or steroid phosphates are not immunogenic and methods for linking substances of either of these classes to immunogenic natural or modified proteins to form novel hapten-protein complexes and conjugates are a further aspect of this invention, as are the novel hapten-protein conjugates themselves.

The lower alkyl groups occurring in the lower alkyl phosphonothioates according to this invention and in the compositions of matter according to this invention are preferably branches or straight chain alkyl groups containing from 1 to 6 carbon atoms. The groups are most preferably methyl or ethyl.

The lower alkyl phosphonothioyloxy group will link to any carbon atom in the steroid residue other than a carbon atom forming a ring junction, i.e. the carbon atoms which are conventionally numbered as 5, 8, 9, 10, 13 and 14. It is believed that steric hinderance prevents reaction at these sites.

In aqueous solution, the haptens of this invention exist in anionic form at pH above about 4, and we have found that they readily form immunogenic water-insoluble complexes when brought into contact with aqueous solutions of esterified proteins such as, for example, methylated bovine serum albumin. The "electrostatic complexes" form because of electrostatic attraction that occurs between cationic esterified protein and anionic hapten.

It is also possible to form covalent immunogenic conjugates from the sulphate mimics. A preparative route to these immunogens involves activation of the mimics by reagents known in the art for this purpose, such as the carbodiimides and chloroformate esters, followed by reaction of the activated products with the nucleophilic centres of natural or modified proteins. In this way the hapten that is structurally mimicking a steroid sulphate is combined covalently with the protein directly through the sulphate-mimicking function. The derived immunogens constitute a class of substances that are distinct from the electrostatic complexes of esterified protein and sulphate mimic. Immunogens formed by the carbodiimide-promoted conjugation of oestrone-3-phosphate with bovine serum albumin are examples of this class.

When administered to animals by known immunization procedures (typically with Freund's Complete Adjuvant) these electrostatic complexes or covalent conjugates will initiate the formation of antibodies displaying unique specificity. For instance, they will bind directly with the "sulphate mimic" used to raise them, with the steroid sulphate that is being mimicked and, to an extent that varies according to the animal in question, with the free steroid; binding with other substances does not occur to any significant extent.

Antisera produced by immunization of animals with the electrostatic complexes or covalent conjugates also fall within the scope of the invention. Such antisera have potentially wide application to radio-immunoassay in the fields of animal and human endocrinology, animal physiology and human pathology. Envisaged uses include pregnancy diagnosis in the pig; the prediction of, say, dystokia, calf numbers, calf growth rates and calf milk production pre-parturition; the detection of human endometrial cancer; the facilitation of human artificial insemination, and for general research into the endocrimology of steriod sulphates.

Further aspects of the invention are illustrated by the following examples:

EXAMPLE 1

Preparation of steroid lower alkylphosphonothioates

The steroid lower alkylphosphonothioates of the invention are prepared by a process comprising reacting a lower alkyldihalophosphonothioate, preferably methyldichlorophosphonothioate, dissolved in an anhydrous organic tertiary base such as pyridine, with a steroid alcohol or phenolic steroid. The conditions are selected to maximize condensation of the steroid with only one of the two reactive halogen atoms of the phosphorus reagent. Accordingly condensation conditions are facilitated by employing a stoichiometric excess of the phosphorus reagent, by slowly bringing the steroid into contact with the phosphorus reagent rather than the reverse, and by allowing the initial stages of the condensation to occur at a temperature of about 0°–4° C. In these circumstances, treatment of the pyridine solution with water after the reaction has been allowed to proceed to completion, followed by acidification, allows for the isolation of steroid monoesters with methylphosphonothioic acid.

Lower alkylphosphonothioates so prepared may readily be converted by conventional methods to form the corresponding esters of related steroids, thereby offering a convenient route to the monoesters of polyhydroxy steroids.

Oestrone-3-methylphosphonothioate was prepared as follows: Oestrone($E_1$) (2.2 g) dissolved in pyridine (18 ml) was added dropwise over 1 hr to a stirred solution of methyldichlorophosphonothioate (3.6 g) in pyridine (18 ml) that was cooled by an ice bath. After the addition, the ice bath was removed and stirring at ambient temperature continued for 24 hr.

The solution was poured into ice water and the precipitate formed was collected by filtration.

Concentration of the pyridine solution at the rotary evaporator resulted in the precipitation of a further yield of product and precipitation was completed by adjusting the solution to pH 2 dropwise addition of 10% hydrochloric acid.

The crude product fractions were combined, suspended in warm water (40° C.) and dissolved by adjusting the solution to pH 8.5. The aqueous solution formed was extracted with ethyl acetate and then adjusted to pH 2.0 to precipitate the product. Oestrone-3-methylphosphonothiate (1.8 g) was obtained as a hemihydrate after crystallization from methanol-water. It had mp 95°–8° C. after which it partly recrystallized and melted again at 157°–60° C.

EXAMPLE 2

Dehydroepiandrosterone-3-methylphosphonothioate

Dehydroepiandrosterone (DHEA) (1.1 g) in dry pyridine (11 ml) was added dropwise over 40 min. to a stirred solution of methyldichlorophosphonothioate (1.8 g) in dry pyridine (11 ml) that was cooled in ice. The ice bath was removed and the solution stirred at ambient temperature for 24 hr.

The solution was poured into ice water and the insoluble products which precipitated were collected by filtration.

Concentration of the pyridine solution at a rotary evaporator and adjustment of the solution to pH 2 gave a further small yield of insoluble product. The combined solid fractions were suspended in warm water (40° C.) and the solution adjusted to pH 8.5. Neutral, insoluble steroids were removed by filtration and the clear filtrate adjusted to pH 2 with dilute hydrochloric acid to precipitate the acid product. Dehydroepiandroesterone-3-methylphosphonothioate (350 mg m.p. 181°–4° C.) was obtained as a hemihydrate after crystallization from methanol-water.

EXAMPLE 3

17β-Oestradiol-3-methylphosphonothioate

To oestrone-3-methylphosphonothioate (364 mg) in ethanol (10 ml) stirred at 0°–4° C. in an ice bath was added a solution of sodium borohydride (240 mg) in ethanol (15 ml) dropwise over 15 min. The solution was stirred a further 2.5 hr in the ice bath then glacial acetic acid added dropwise to remove excess borohydride reagent.

The ethanol was removed by evaporation; the residue was dissolved in water, cooled in ice and acidified to pH 2 with 10% hydrochloric acid. The precipitated product was collected and washed with excess water; after crystallization from ethanol-water, 17β-oestradiol-3-methyl-phosphonothioate was obtained as a chromatographically homogeneous product (180 mg; m.p. 124°–127° C., after drying at 1 mm, 50° C., 50 hr).

EXAMPLE 4

Electrostatic Complex of Oestrone-3-methylphosphonothioate and Methyl-esterified Bovine Serum Albumin (MBSA)

Oestrone-3-methylphosphonothioate (40 mg) was suspended in water (10 ml), dissolved by slowly adjusting the solution to pH 7.5, and added dropwise with stirring over 5 min to a solution with dilute NaOH of methyl-esterified bovine serum albumin (MBSA, 140 mg) in water (15 ml) at pH 7.5. The complex commenced to precipitate when about 70% of the steroid derivative had been added. When the steroid addition was complete, stirring at room temperature was continued (20 min) and the suspension then kept at 4° C. (1-16 hr).

The precipitate was collected by centrifugation, washed with water and dried by lyophilization. Yield 105 mg.

By using $^3$H-oestrone-3-methylphosphonothioate tracer, the incorporation of hapten in the isolated electrostatic complex could be determined and was found to be 38 moles/mole MBSA.

Esterified proteins, such as MBSA, are prepared by procedures known in the art. A typical method would be to treat a serum albumin with an excess of methanol containing hydrochloric acid at a final concentration of 0.1 N, at a temperature of 15°–25° C. Preferably the esterification should be allowed to proceed for at least 24 hours but for no more than about 72 hours - at shorter periods it has been found that the product does not readily form electrostatic complexes with the haptens, while more protracted treatments tend to give rise to esterified proteins which form electrostatic complexes of reduced immunogenicity.

EXAMPLE 5

Conjugation of Oestrone-3-methylphosphonothioate to Bovine Serum Albumin (BSA)

Oestrone-3-methylphosphonothioate (72 mg) in dioxan (10 ml) was treated with a solution of 1-ethyl-3-(3-dimethylaminopropyl) carbodiimide hydrochloride (38 mg) in water (3.2 ml) and stirred at ambient temperature (30 min). BSA (72 mg) in phosphate buffer (0.05 M, pH 7.8, 10 ml) was added and stirring maintained. After 24 hr the solution was dialysed at 4° C. against water and lyophilized.

Yield of conjugate was 65 mg, containing 14 moles steroid per mole protein.

EXAMPLE 6

Conjugation of oestrone-3-phosphate to Bovine Serum Albumin (BSA)

Oestrone-3-phosphate (100 mg) in dioxan (10 ml) was treated with a solution of 1-ethyl-3-(3-dimethylaminopropyl) carbodiimide hydrochloride (165 mg) in water (5 ml) and stirred at ambient temperature (30 min). BSA (200 mg) in phosphate buffer (0.05 M, pH 7.8, 10 ml) was added in one portion and stirring maintained. After 24 hr the solution was dialysed at 4° C. against phosphate buffer (0.01 M, pH 7.4) and lyophilized.

By using a $^3$H-oestrone-3-phosphate tracer the incorporation of hapten was found to be 8 moles/mole BSA.

EXAMPLE 7

Electrostatic Complex of Dehydroepiandrosterone-3-methyl-phosphonothioate and Methyl-esterified Bovine Serum Albumin Using a procedure identical to that given in Example 4, the title complex (110 mg) was obtained containing 22 moles steroid per mole of MBSA.

EXAMPLE 8

Immunization of Animals

Complexes or conjugates were suspended in saline (1.5 mg/ml) and emulsified with an equal volume of Freund's complete adjuvant (FCA). These emulsions were re-emulsified with a further volume, equal to the original saline volume, of 1% aqueous Tween 80. Injections of 1.5 mg of the immunogens of the invention in 3 ml emulsion were given to each animal, with 1 ml intramuscularly into each hind leg and 1 ml subcutaneously over six lumbar sites. Injections were repeated at monthly intervals. Blood was taken by jugular venepuncture, sera allowed to separate, centrifuged and stored below −10° C.

Using the elecgrostatic complex of Example 4, anti-oestrone sulphate antibody titres of 1:500 to 1:13,000 were observed typically in immunized sheep.

Using the covalent conjugate of Example 5 anti-oestrone sulphate antibody titres of 1:500 to 1:10,000 were observed typically in immunized sheep.

Using the covalent conjugate of Example 6 anti-oestrone sulphate antibody titres of 1:100 to 1:800 were observed typically in immunized sheep.

Using the electrostatic complex of Example 7 antidehydroepiandrosterone sulphate antibody titres of 1:200 to 1:1500 were observed typically in immunized sheep.

Antibody titre is defined here as the dilution of the antiserum which binds 50% of the maximum amount of labelled steroid bound by the antiserum during incubation of about 50 picograms of steroid for about 18 hours at 4° C., followed by the use of either dextran-coated charcoal or polyethylene glycol to separate free from antibody-bound steroid.

Cross-reactions of an antiserum formed in response to the immunogen of Example 4 were as follows:

| Steroid | % Cross-reaction |
| --- | --- |
| Oestrone-3-methylphosphonothioate | 100 |
| Oestrone sulphate | 100 |
| Oestrone (E$_1$) | 57 |
| 2-Hydroxy-E$_1$ (with ascorbic acid) | 9 |
| 2-Hydroxy-E$_1$ (no ascorbic acid) | 1.1 |
| 17β-Oestradiol | 0.5 |
| 3,16α,17β-Oestriol | <0.1 |
| 17β-Oestradiol-3-sulphate | <0.1 |
| Oestrone-3-glucosiduronate | 3.2 |
| DHEA - sulphate | <0.1 |
| DHEA | <0.1 |
| DHEA - glucosiduronate | <0.1 |
| 5α-Androsterone-3-sulphate | <0.1 |
| Testosterone | <0.1 |
| 4-Androstene-3,17-dione | <0.1 |
| Progesterone | <0.1 |
| 17-Hydroxyprogesterone | <0.1 |
| Cortisol | <0.1 |
| Pregnenolone-3β-sulphate | <0.1 |
| 5β-Pregnane-3α,20α-diol-3α-glucosiduronate | <0.1 |

EXAMPLE 9

Plasma Radioimmunoassay of Oestrone-3-Sulphate (a) Samples of plasma (0.05, 0.1, or 0.2 ml) were added to assay tubes containing 0.1 ml PBS (phosphate-buffered saline; 0.1 M sodium phosphate, pH 6.8, containing (w/v) 0.9% NaCl, 0.1% sodium azide) or 0.1 ml [$^3$H]oestrone sulphate (1,000 dpm) in PBS. After the addition of 0.5 ml 3 M NaCl, the samples were mixed thoroughly and allowed to equilibrate for 30 min at 25° C. The samples were extracted once with 4 ml ether and the ether extract was discarded. The samples were then extracted twice with 4 ml ethyl acetate and the ethyl acetate extract was transferred to tubes for assay or scintillation vials to assess recovery, dried under N$_2$, and redissolved in 0.1 ml PBS.

(b) Antiserum (0.1 ml 1:2,000 dilution in PBS) and [$^3$H]oestrone sulphate (10,000 dpm or 50 pg in 0.1 ml PBS) were added to samples and standards, mixed thoroughly, and incubated at 4° C. for 18–24 h. Bound and free steroids were separated by centrifugation (2,500×g) after incubation with 1 ml dextran-coated charcoal (0.5% Norit and 0.1% dextran in PBS) for 5 min at 4° C. The supernatant was decanted, mixed with a scintillant solution and the radioactivity counted. Under the same assay conditions an appropriate calibration graph was constructed with known amounts of oestrone-3-sulphate and from this the quantity of oestrone-3-sulphate in the plasma was determined.

This procedure is applicable to a wide range of biological fluids including milk, urine, cell culture media as well as to blood plasma and serum. With some species (e.g. cattle, sheep, pig, horse) the assay can often be carried by mixing about 1–50 μl of the plasma directly with the antiserum at stage (b). In this case the calibration curve samples include the corresponding volume of plasma from an ovariectomized animal of the same species.

We claim:

1. A lower alkyl phosphonothioate of a steroid alcohol or phenolic steroid, having the formula

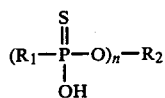

wherein $R_1$ is lower alkyl; $R_2$ is a steroid residue, each phosphonothioyloxy group being joined to a carbon atom of the steroid nucleus other than one of the carbon atoms forming a ring junction, or to a side chain carbon atom; and n is an integer from 1 to 4.

2. Oestrone-3-methylphosphonothioate, a compound as claimed in claim 1 in which $R_1$ is methyl, $R_2$ is oestrone linked to the rest of the molecule through its number 3 carbon atom and n is 1.

3. Dehydro-epiandrosterone-3-methylphosphonothioate, a compound as claimed in claim 1 in which $R_1$ is methyl, $R_2$ is dehydroepiandrosterone linked to the rest of the molecule through its number 3 carbon atom and n is 1.

4. Oestra-3,17-diol-3-methylphosphonothioate, a compound as claimed in claim 1 in which $R_1$ is methyl, $R_2$ is 17 β-oestra-diol, linked to the rest of the molecule through its number 3 carbon atom and n is 1.

5. A process for preparing a lower alkylphosphonothioate of a steroid alcohol or phenolic steroid, having the formula

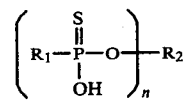

wherein $R_1$ is lower alkyl; $R_2$ is a steroid residue, each phosphonothioyloxy group being joined to a carbon atom of the steroid nucleus other than one of the carbon atoms forming a ring junction, or to a side chain carbon atom; and n is an integer from 1 to 4, said process comprising reacting a lower alkyl dihalophosphonothioate with a steroid alcohol or phenolic steroid having the formula $(HO)_n\text{–}R_2$, wherein $R_2$ is a steroid residue, each hydroxyl group being joined to a carbon atom of the steroid nucleus other than one of the carbon atoms forming a ring junction, or to a side chain carbon atom; and n is an integer from 1 to 4.

6. A process according to claim 5, which comprises reacting the steroid alcohol or phenolic steroid with a stoichiometric excess of a lower alkyldihalophosphonothioate, in an anhydrous organic basic solvent.

7. A compound according to claim 1, wherein $R_1$ is methyl or ethyl.

8. A compound according to claim 1, wherein n is 1.

9. A process according to claim 5, wherein said lower alkyldihalophosphonothioate is methyldichlorophosphonothioate.

10. A process according to claim 9, wherein said solvent is pyridine.

11. A compound according to claim 1, which is a phenolic steroid having the same carbon skeleton as oestrone.

12. A compound according to claim 1, which is a steroid alcohol having the same carbon skeleton as dehydroepiandrosterone.

13. A compound according to claim 1, which is a steroid alcohol having the same carbon skeleton as pregnenolone.

14. A process according to claim 5, wherein n is 1.

* * * * *